US012752231B2

(12) United States Patent
Emwas et al.

(10) Patent No.: US 12,752,231 B2
(45) Date of Patent: Oct. 6, 2026

(54) PORTABLE BREATHING AIR FILTERING DEVICE AND METHOD

(71) Applicant: KING ABDULLAH UNIVERSITY OF SCIENCE AND TECHNOLOGY, Thuwal (SA)

(72) Inventors: Abdul-Hamid Mohammed Emwas, Thuwal (SA); Osama Shekhah, Thuwal (SA); Mohamed Essam Fayez Awad Hagar, Alexandria (EG); Mohamed Eddaoudi, Thuwal (SA); Nikolaos Papagiannis, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 303 days.

(21) Appl. No.: 18/271,724

(22) PCT Filed: Jan. 6, 2022

(86) PCT No.: PCT/IB2022/050091
§ 371 (c)(1),
(2) Date: Jul. 11, 2023

(87) PCT Pub. No.: WO2022/157588
PCT Pub. Date: Jul. 28, 2022

(65) Prior Publication Data

US 2024/0058738 A1 Feb. 22, 2024

Related U.S. Application Data

(60) Provisional application No. 63/290,144, filed on Dec. 16, 2021, provisional application No. 63/139,585, filed on Jan. 20, 2021.

(51) Int. Cl.
*B01D 47/02* (2006.01)
*A61L 9/014* (2006.01)
(Continued)

(52) U.S. Cl.
CPC .............. *B01D 47/02* (2013.01); *A61L 9/014* (2013.01); *A61L 9/145* (2013.01); *B01D 47/021* (2013.01);
(Continued)

(58) Field of Classification Search
CPC ....... B01D 47/00; B01D 47/02; B01D 47/021
See application file for complete search history.

(56) References Cited

U.S. PATENT DOCUMENTS

2018/0221806 A1 8/2018 Fang

FOREIGN PATENT DOCUMENTS

CN 2624905 7/2004
CN 104121644 A * 10/2014
(Continued)

OTHER PUBLICATIONS

Communication under Rule 164(2)(a) EPC, in corresponding/related European Application No. 22700154.2, dated Jul. 18, 2024.
(Continued)

*Primary Examiner* — Robert A Hopkins
(74) *Attorney, Agent, or Firm* — PATENT PORTFOLIO BUILDERS PLLC

(57) ABSTRACT

An air breathing filtering system includes a housing having an air input and an air output, a first filtering stage that filters out particles from a first air stream to generate a second air stream, and a second filtering stage that filters out germs from the second air stream to generate a third air stream, wherein the second filtering stage uses a different filtering process than the first filtering stage. The first air stream is received at the air input and the third air stream is discharged outside the housing at the air output. The second filtering stage uses a liquid to disable the germs from the second air stream.

17 Claims, 11 Drawing Sheets

(51) Int. Cl.
*A61L 9/14* (2006.01)
*B01D 50/60* (2022.01)
*F24F 8/24* (2021.01)

(52) U.S. Cl.
CPC ................ *B01D 50/60* (2022.01); *F24F 8/24* (2021.01); *A61L 2209/14* (2013.01); *A61L 2209/16* (2013.01); *B01D 2279/50* (2013.01); *B01D 2279/65* (2013.01)

(56) References Cited

FOREIGN PATENT DOCUMENTS

| | | | |
|---|---|---|---|
| CN | 108050622 A | | 5/2018 |
| CN | 210057787 U | * | 2/2020 |

OTHER PUBLICATIONS

International Search Report in corresponding/related International Application No. PCT/IB2022/050091, date of mailing Jun. 23, 2022.

Invitation to Pay Additional Fees and, Where Applicable, Protest Fee in corresponding/related International Application No. PCT/IB2022/050091, date of mailing Apr. 29, 2022.

Written Opinion of the International Searching Authority in corresponding/related International Application No. PCT/IB2022/050091, date of mailing Jun. 23, 2022.

* cited by examiner

| Species | Size (nm) |
| --- | --- |
| Viruses | viruses vary greatly in size, from 20 to 150 nm in diameter |
| | COVID-19 virus size (65-125 nm in diameter) |
| $O_2$ | 0.346 |
| $N_2$ | 0.364 |
| $CO_2$ | 0.330 |

FIG. 1

PORTABLE BREATHING AIR FILTERING DEVICE AND METHOD

CROSS-REFERENCE TO RELATED APPLICATIONS

This application is a U.S. National Stage Application of International Application No. PCT/IB2022/050091, filed on Jan. 6, 2022, which claims priority to U.S. Provisional Patent Application No. 63/139,585, filed on Jan. 20, 2021, entitled "PORTABLE BREATHING AIR FILTERING DEVICE AND METHOD," and U.S. Provisional Patent Application No. 63/290,144, filed on Dec. 16, 2021, entitled "PORTABLE BREATHING AIR FILTERING DEVICE AND METHOD," the disclosures of which are incorporated herein by reference in their entirety.

BACKGROUND

Technical Field

Embodiments of the subject matter disclosed herein generally relate to a system and method for removing viruses and/or bacteria from air, and more particularly, to a system that is portable, can be deployed to any desired location, and is capable to remove dangerous viruses and/or bacteria to provide safe breathing air.

Discussion of the Background

The recently unexpected explosion of the COVID-19 pandemic, coupled with the suffering of millions of infected patients fighting the SARS-COV-2-19 virus, without any proven efficient treatment so far, emphasizes the absolute need to develop effective ways to prevent the spread of this and other viruses. Although many aspects of the COVID-19 are still debated among the scientists including the severity with which different organs are attacked by the virus, the long terms consequences to the human health, and the transition route of the virus, there is increasing evidence that the virus is transmitted through droplets that are airborne. Thus, closed areas such as transportation means, rooms, classrooms, and offices with inadequately ventilated environments present a very high-risk factor for the spread of the SARS-COV-2-19 virus.

Therefore, filtering and cleaning the breathing air from the viruses is considered an important approach to control this pandemic, because it is not only important for reducing the spread of the disease, but also it is crucial to save human lives. There are many air filters on the market today, like face masks that are believed to reduce the propagation of the virus. Each of these air filters has a certain efficiency, as they rely on one or more layers of a porous solid material, which is expected to stop the virus because the size of the pores is smaller than the size of the virus. While these static air filters are effective, they have some limitations like, they are efficient most of the time, but not all the time, they can be used only for a limited number of times, some of the subjects using these air filters report breathing problems, and they are also a source of infection if not handled properly.

More dynamic means for destroying the virus involve the use of ultraviolet light, which has a wavelength close to the wavelength that destroys the virus. However, this approach is dangerous if the human beings are in direct contact with the ultraviolet light, as it is known that this type of light destroys the cornea in the eye. Therefore, special care needs to be exercised when this procedure is deployed for cleaning an enclosure.

Another means for destroying the virus involve the use of chemical products or alcohol directly on the human skin or surfaces with which the humans interact as these chemical compounds are effective in annihilating the virus. However, these chemical compounds are also known to negatively affect the humans and the environment and thus, it is undesired to have such a direct contact between them and humans or the environment.

Thus, there is a need for a new system and method that is capable of destroying the virus before it enters the human body, meanwhile it is not dangerous for humans, and can be deployed wherever necessary, without large investments.

BRIEF SUMMARY OF THE INVENTION

According to an embodiment, there is an air breathing filtering system that includes a housing having an air input and an air output, a first filtering stage that filters out particles from a first air stream to generate a second air stream, and a second filtering stage that filters out germs from the second air stream to generate a third air stream, wherein the second filtering stage uses a different filtering process than the first filtering stage. The first air stream is received at the air input and the third air stream is discharged outside the housing at the air output. The second filtering stage uses a liquid to disable the germs from the second air stream.

According to another embodiment, there is an air conditioning, AC, system for cooling or heating air. The air conditioning system includes an AC unit configured to heat or cool an air stream, and an air breathing filtering system fluidly attached to the AC unit, and configured to remove germs from the air stream. The air breathing filtering system includes a first filtering stage that filters out particles from a first air stream to generate a second air stream, and a second filtering stage that filters out germs from the second air stream to generate the air stream, wherein the second filtering stage uses a different filtering process than the first filtering stage. The second filtering stage uses a liquid to disable the germs from the second air stream.

According to yet another embodiment, there is a method for disabling germs from an air stream, and the method includes receiving a first air stream, filtering out, with a first filtering stage, particles from the first air stream to generate a second air stream, and filtering out, with a second filtering stage, germs from the second air stream to generate a third air stream. The second filtering stage uses a different filtering process than the first filtering stage and the second filtering stage uses a liquid to disable the germs from the second air stream.

BRIEF DESCRIPTION OF THE DRAWINGS

For a more complete understanding of the present invention, reference is now made to the following descriptions taken in conjunction with the accompanying drawings, in which:

FIG. 1 illustrates the sizes of the viruses and the SARS-COV-2-19 virus and various air components;

DETAILED DESCRIPTION OF THE INVENTION

Figure 2:
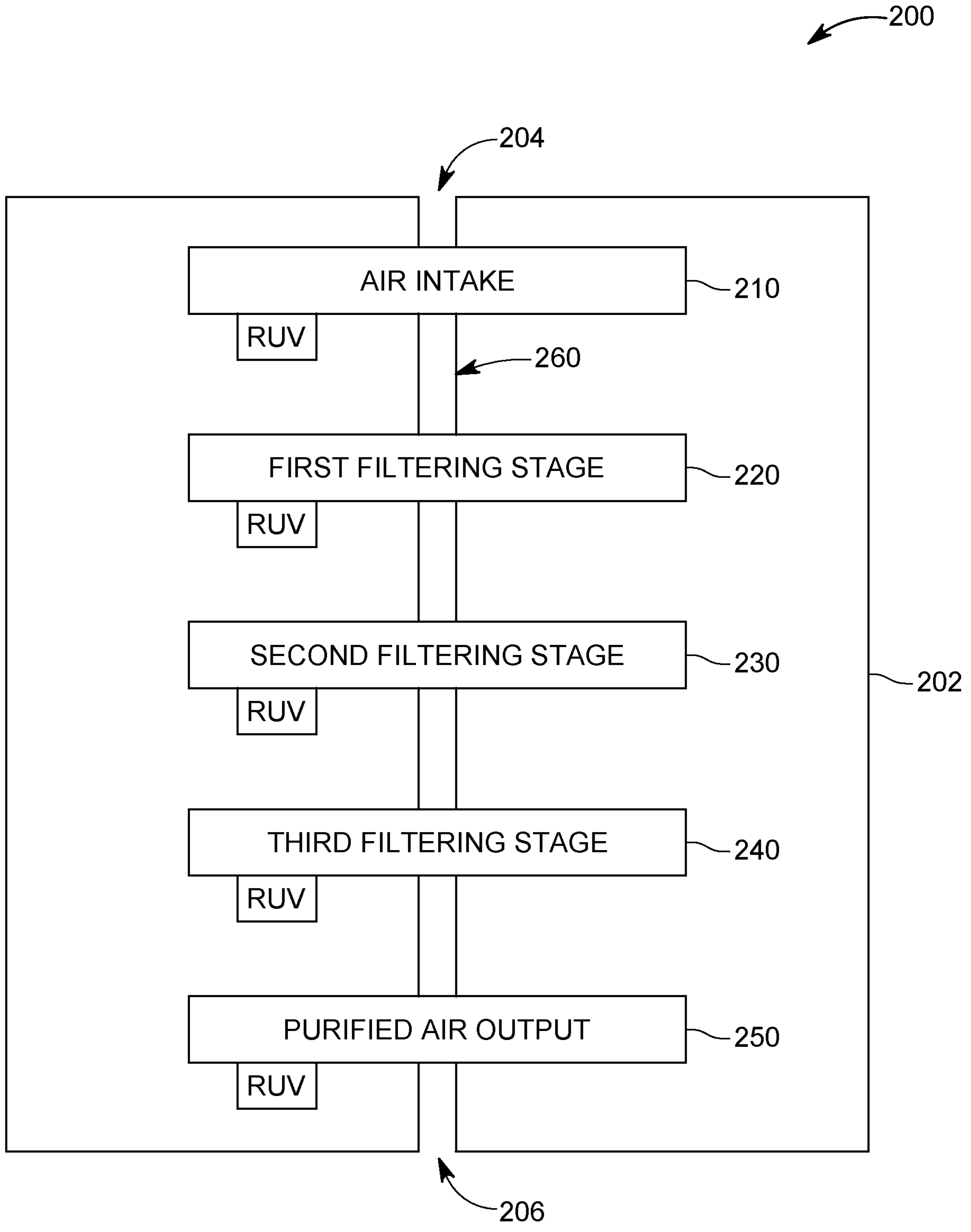
FIG. 2 schematically illustrates the components of an air breathing filtering system that uses plural filtering stages, one of which is based on a fluid.

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to a portable breathing air filtering system that can be attached to existing air conditioning (AC) system for removing germs (i.e., viruses and/or bacteria) from the cooled or heated air. However, the embodiments to be discussed next are not limited to a portable system, but may be applied to any system or it may be a standalone system, which is not attached to an AC system.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, an air breathing filtering system directs an incoming air stream along a specific path, so that the incoming air stream encounters two or more filtering means for removing the germs from the air. The filtering means may include a passive filtering device (i.e., a device that has no moving parts) and a dynamic filtering device (i.e., a device that has at least one moving part). More than two filtering devices may be placed along the path of the air stream. The entire air breathing filtering system is compact, may be located in a single housing, and may be portable, i.e., moved from one location to another location. The air breathing filtering system may be a standalone system or may be used in conjunction with an existing AC system. The air breathing filtering system may be manufactured to be small enough to be attached to a vehicle, airplane, train, etc.

The air breathing filtering system is expected to have one or more of the following advantages: it can be easily fit into the existing ACs of buildings, vehicles, etc. to be used onboard any moving vehicle to clean the air from germs, it is possible to manufacture it as a separate mobile/portable device that can be used to filter and clean the air. The system can also be used in any closed area/confined spaces such as classrooms, lecture halls, offices, meeting room, busses, ships and aircrafts, and the system can be modified to be scaled up to be used in large open areas such as Metro stations, airports, hospitals corridors and medical centers.

The inventors have observed that the differences between the air particle sizes and the germs size, specifically the SARS-Cov-2-19 virus are significant, i.e., the virus' size is three order of magnitude larger than the air components, as indicated in the table in FIG. 1. Based on these observations, the inventors have developed an air breathing filtering system that uses in addition to a filtering device, antiviral and/or antimicrobial drugs coated/encapsulated on/in porous materials as an additional filtering device. For example, a thin film of these materials with pre-defined properties (i.e., pore size) is fabricated via different approaches, as discussed later, as freestanding films or on other supports for enhancing the filtering function of the first filtering device. The porous material allow only the air particles to pass through while filtering the germs. Additionally, the coated/encapsulated antimicrobial drugs on/in these porous materials kill the germs and/or further degrade the germ's components.

As schematically illustrated in FIG. 2, the novel air breathing filtering system 200 has the following stages: an air intake stage 210 that is configured to pull in air from outside the system (first air stream), a first filtering stage 220 that removes from the first air stream large pollutants, such as dust and large size germs, and generate a second air stream, a fluid-based second filtering stage 230, which treats the second air stream with one or more antivirus and/or anti-microbial and/or alcohols, and/or detergent based substances (e.g., drugs) and which generates a third air stream, an optional third filtering stage 240 that may include additional filtering means, e.g., electrostatic, UV light, etc. and treats the third air stream, and an air output unit that discharges the purified air outside the system 200. All the stages are placed within a housing 202, which is movable to any desired location. An input 204 formed in the housing 202 connects the ambient air to a conduit system 260, that fluidly connects the stages noted above. In one application, the conduit system 260 connects the above noted stages in the order introduced in this paragraph. In this or another applications, the stages are connected in series by the conduit system. An output 206 is also formed in the housing 202 and is configured to discharge the purified air to the desired location.

Figure 3A:
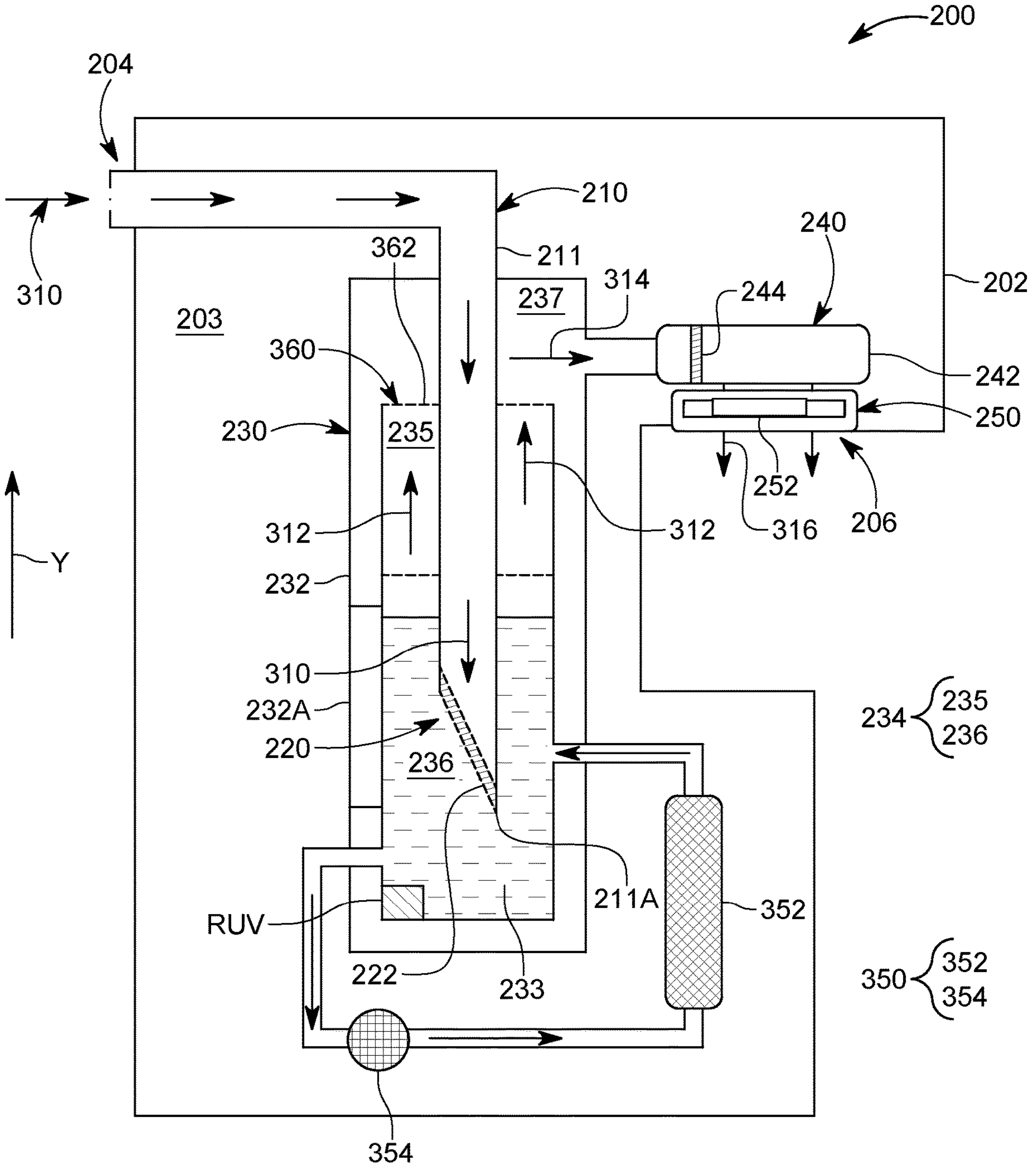
FIG. 3A shows a detailed configuration of the components of an air breathing filtering system that uses several filtering stages, one of which is based on a fluid.

One possible implementation of the air breathing filtering system 200 is now discussed with regard to FIG. 3A. The system 200 has the air intake stage 210 fluidly connected to an internal container 232. The internal container 232 may be made of plastic, composite, metal or any other material that is capable of holding a liquid. The internal container extends along a vertical axis Y inside the housing 202. In one application, the entire container 232 is located inside the housing 202. The space 203 between the container 232 and the housing 202 is filled with air or with an insulating material. The container 232 holds a fluid 233 in an internal chamber 234 so that an upper part 235 of the internal chamber 234 is free of the fluid, and a lower part 236 of the chamber is full with the fluid 233. The air intake stage 210 may include a pipe 211 that extends into the fluid 233 in the chamber 234, through the entire upper part 235 and partially into the lower part 236, as shown in the figure. This means that an end 211A of the pipe 211 is located inside the fluid 233. The pipe 211 is configured to absorb a first air stream 310 from outside the housing 202, and deliver the first air stream directly into the fluid 233. The above discussed configuration can be modified to include plural chambers 234, for example, a first chamber holding a concentrated alcohol while a second chamber holding water with detergents. Any number of chambers with any holding fluid may be added to the embodiment illustrated in FIG. 3A.

The first filtering stage 220 is located at the end 211A of the pipe 211 and may be a static air filter 222 having a pore size selected to be in a range of 2-5 μm, to filtrate large pollutants such as dust and large size microbial species. The air filter 222 may be made of any porous material having the pore's size noted above. In one application the air filter 222 may be coated with a water repellent substance or may be made of a material that is hydrophobic, so that the fluid 233 cannot pass through the air filter 222, into the pipe 211. However, even if the fluid 233 passes through the air filter 222 into the pipe 211, the functionality of the system is not affected. A door 232A may be provided in a wall of the container 232 so that if necessary, the air filter 222 may be replaced and other maintenance routines may be performed inside the chamber 234.

The fluid 233 may include one or more of the following chemical compounds and/or elements. One possible chemical compound is alcohol. Alcohols such as ethanol and isopropanol are the most commonly used sanitizers. For example, 70% of an ethanolic solution is widely used in biological labs for disabling germs. It is well documented that ethanol at 60-80% concentration is a powerful agent to deactivate lipophilic viruses such as herpes and influenza viruses. The main mechanism to explain this is that the alcohols affects proteins, which are very effective and relevant for the SARS-Cov-2 virus. Due to the denaturation of the surface proteins, the virus loses its ability to enter the human cells, as the virus uses a spike glycoprotein to bind to host cell sialic acid receptors. However, alcohols are flammable liquids that could be ignited if used near a flame, spark or any ignition source, particularly when the alcohols are applied by spraying as a mist. Most importantly, since the alcohols are volatiles solvents, they cause short time antiviral effects, and frequent use of alcohols is necessary to achieve the desired effects. This makes alcohols usage a temporary solution, but costly as well as posing safety and environmental concerns. However, by holding the alcohol inside the chamber 234, these disadvantages are reduced as the alcohol has a limited space where to evaporate, it is protected from unwanted ignition, and it is prevented from directly interacting with humans or the environment.

The chemical compound may include one or more detergents. In this regard, the detergents were proven to be potent veridical agents for several viruses. However, the veridical effect is dependent on the pH value. Differences in veridical activity of the detergents were determined according to the effects of the pH on its ionic state on the viral capsid proteins. On the other hand, some detergents are irritant and can cause local tissue irritation to the skin, eyes, oral and respiratory mucosa. Aspiration and dermal irritation, and potentially burns, are possible complications from detergent exposure. Moreover, the dumping of millions of tons of detergents solutions on the urban streets lead to severe environmental effects that have deleterious impact on soil, water and plants. However, these negative effects are minimized for the system 200 as the detergent is kept inside the chamber 234, and does not interact with the humans or the medium outside the chamber. Because the detergent is also insulated from the humans and the ambient, any concentration of the detergents may be used inside the chamber 234.

In yet another embodiment, the chemical compound may be a bleaching agent. Bleaching agents are another class of chemicals that are effective in deactivating the S-protein of the viruses and they inhibit their mode of action. However, the difference in chemical structures of such compounds affects the degree of disinfection action and also their biocide activity, which is relevant to the surface/water disinfection. In this regard, most of the bleaching agents possess high negative influence on human health when a human is exposed to a large dose, for example, chloro-compounds are considered as cancerous agents. Moreover, most of the bleaching agents have strong oxidizing properties and spilling high-concentration peroxide solutions on flammable substances can cause an immediate fire. While the sodium hypochlorite in an aqueous solution is not explosive, the anhydrous sodium hypochlorite is an explosive substance. Although calcium hypochlorite is not flammable, it acts as an oxidizer with combustible materials. Again, because of the nature of the closed environment in the chamber 234 in which the bleaching agent is hold, there is almost no danger for humans to use such agents in the system 200, no matter the concentration of the bleaching agent.

An anti-microbial drug is another substance that can be used in or as the fluid 233. Different types of antiviral composites are being studied and tested in the fight against the germs. These antiviral composites have a mechanism that include rupturing the virus envelop or deactivating the virus'S-protein. Example of such drugs and/or composites include Ribavirin, Favipiravir, 2'-Fluoro-2'-deoxycytidine, Amodiaquine, Lopinavir, Ritonavir, Ivermectin, Remdesivir, as well as some naturally occurring flavonoids. In fact, any drug may be used inside the chamber 234 for purifying the air stream 310.

The virus rupture mechanism can be implemented with one of two methods. The first method includes the use of a cationic surfactant to hook the anionic surface of the virus and mesoporous material filled with long chain alcoholic compounds for the sensitization step. The second method uses active oxygen liberating elements such as Cu, Ta and Nb that could give a source that will be able to crack the virus envelop or denature its surface protein. Thus, any of the abode discussed chemical compounds may be used in or as the fluid 233.

As the fluid 233 is used up during the filtering process of the air stream 310 as more germs are destroyed, there is a point at which the fluid needs to be either refreshed or replaced. Access through the door 232A may be used to replace the fluid 233. Alternatively, a fluid cleaning system 350 may be implemented to remove the residue (e.g., dead germs, or various chemical compounds formed when the air stream 310 interacts with the fluid) from the fluid 233. The fluid cleaning system 350 may have a filter 352 and a pump 354 that circulates the fluid 233 through the filter 352. The filter 352 may be a mechanical filter, an ultrasonic based filter, a thermal based filter, an electrical filter, a radiation based filter, or a combination of these filters.

An ultrasonic filter is based on generating ultrasound and exposing the germs to such sound. It has been reported that microorganisms and viruses could be removed under the strength of the ultrasonic generated sound. Ultrasonication of dirt water with viruses and microorganisms can generate alternating compression and expansion areas, thereby producing tiny bubble nuclei. Small bubble nuclei that experience shrinkage and instantaneous collapse generate high temperature and high pressure. These actions thereby deactivate viruses and other microorganisms.

A thermal filter is based on raising the temperature of the filter for destroying the germs. In this regard, it is known that the lifetime of SARS-Cov-2 virus is shorter at high temperatures and higher humidity while it survives for longer periods at cooler and dryer environment. Several reports have shown that a raise in the temperature up to 65 C for few minutes leads to elimination of the virus.

An electrical filter is based on generating a pulsed high electric field, which is applied to viruses in a liquid for deactivating the virus. A high-pulsed voltage may be generated between two electrodes and the viral suspension may be continuously transported between the two electrodes, and thus, effectively deactivated. Such electrodes may be used as the filter 352.

A radiation based filter may use ultraviolet C (UVC) wavelengths (100-280 nm) radiation, which is widely used as a disinfectant for water and air. The efficacy of the UVC light against several types of viruses is documented. Recently, UVC was investigated to examine its powerful effect on disabling SARS-CoV-2 viruses, and encouraging results were obtained. However continuous irradiation of public area with UV light is not recommended since exposure to high energy light can be a health hazard that may affect both the skin and the eye. This is not an issue for the system 200 as a radiation based UV filter RUV, which can be attached to any of the stages 220, 230, 240, and 250, as illustrated in FIG. 2, is fully located inside the housing 202, thus shielding the public from the negative effects of this radiation. An UV based filter stage can be implemented as the first and/or third filtering stage. In one implementation, the radiation based UV filter RUV can be placed inside the chamber 234, either in the bottom part 236, as shown in FIG. 3A, or in the top part 235. In one application, the RUV filter can be placed inside the pipe 211, or inside the filter 352, or anywhere inside the system 200. The RUV filter may also be replaced with another device that destroys the germs, for example, an ultrasonicator bath or an electrical device (for example, two electrodes connected to a high voltage) to produce an electrical shock.

After the air stream 310 passes the first filtering stage 220, it becomes air dissolved in the fluid 233. After this air is further processed by the fluid 233 during the second filtering stage 230, with one or more of the chemical compounds discussed above, the air exits the liquid 233 at the top part 235 of the chamber 234, and forms a second air stream 312. The second air stream 312 now arrives at an optional filtering stage 360, which may be implemented as a mechanical filter 362. Other types of filters may be used, as discussed above.

A third air stream 314 is then generated, and this air stream exits the chamber 234 and enters an upper chamber 237, which is defined by the walls of the chamber 234 and the walls of the container 232. Note that the pipe 211 extends through the upper chamber 237, without allowing the incoming air stream 310 to enter directly into the upper chamber 237. The third air stream 314 enters then the third filtering stage 240, which is optional. If the third filtering stage 240 is not present, then the third air stream 314 enters directly into the purified air output 250. In an enclosure/housing 242 of the third filtering stage 240, which is in fluid communication with the upper chamber 237, a filter 244 may be placed to further clean the air stream. The filter 244 may be any of the filters discussed above.

The purified air output 250 is fluidly connected to the third filtering stage 240, and ensures that the fourth air stream 316 is discharged through the output 206, outside the system 200. The purified air output 250 hosts an air suction pump 252 that is configured to ensure that the air streams discussed above move constantly through the system 200. In one embodiment, the air suction pump 252 may be located in another stage of the system 200, for example, in the air intake stage 210.

Figure 3B:
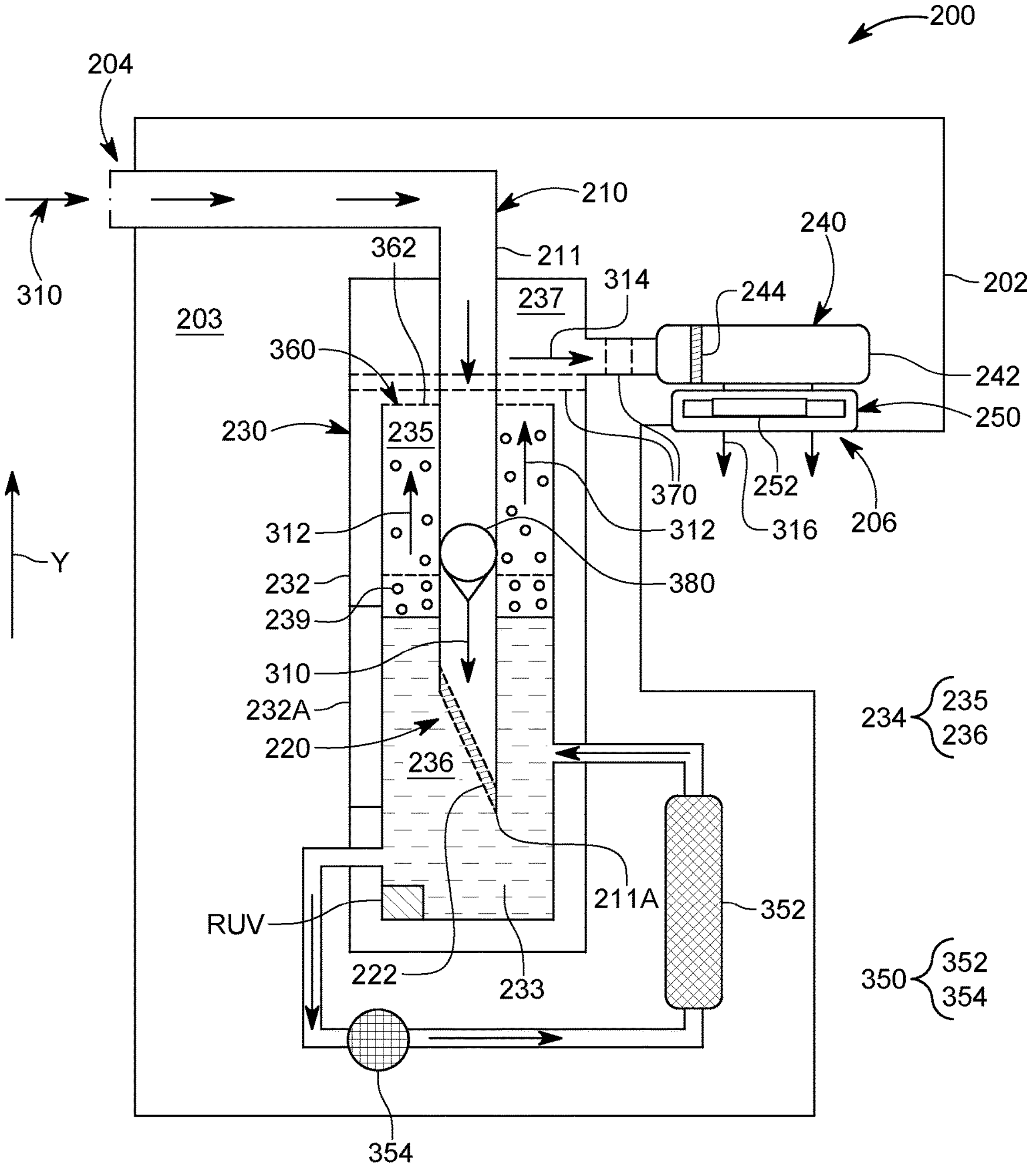
FIG. 3B shows a modified air breathing filtering system that has a demister for removing vapors from the filtered air.

The system 200 illustrated in FIG. 3A may be modified to prevent vapors that form inside the chamber 234 from traveling together with the second air stream 312 to reach the user of the system as the vapors may carry part of the liquid 233, which may be toxic for humans. Note that the vapors 239 typically form at the surface of the liquid 233, in the upper chamber 235, as shown in FIG. 3B. Thus, a demister 370 may be placed either in the upper chamber 237, or just upstream the third filtering stage 240, as also shown in the figure. Note that the demister 370 is optional and if the liquid 233 is not toxic to humans, the demister may be omitted. Any known demister may be used for this embodiment. To also prevent vapors from traveling along the air intake stage 210, opposite to the incoming air stream 310, in one embodiment, as also shown in FIG. 3B, it is possible to place a one-way valve 380 to allow the air stream 310 to move into the chamber 234, but to prevent the vapors 239 to escape through the air intake stage 210. This feature is also optional and may be combined with any of the features discussed herein.

Figure 4:
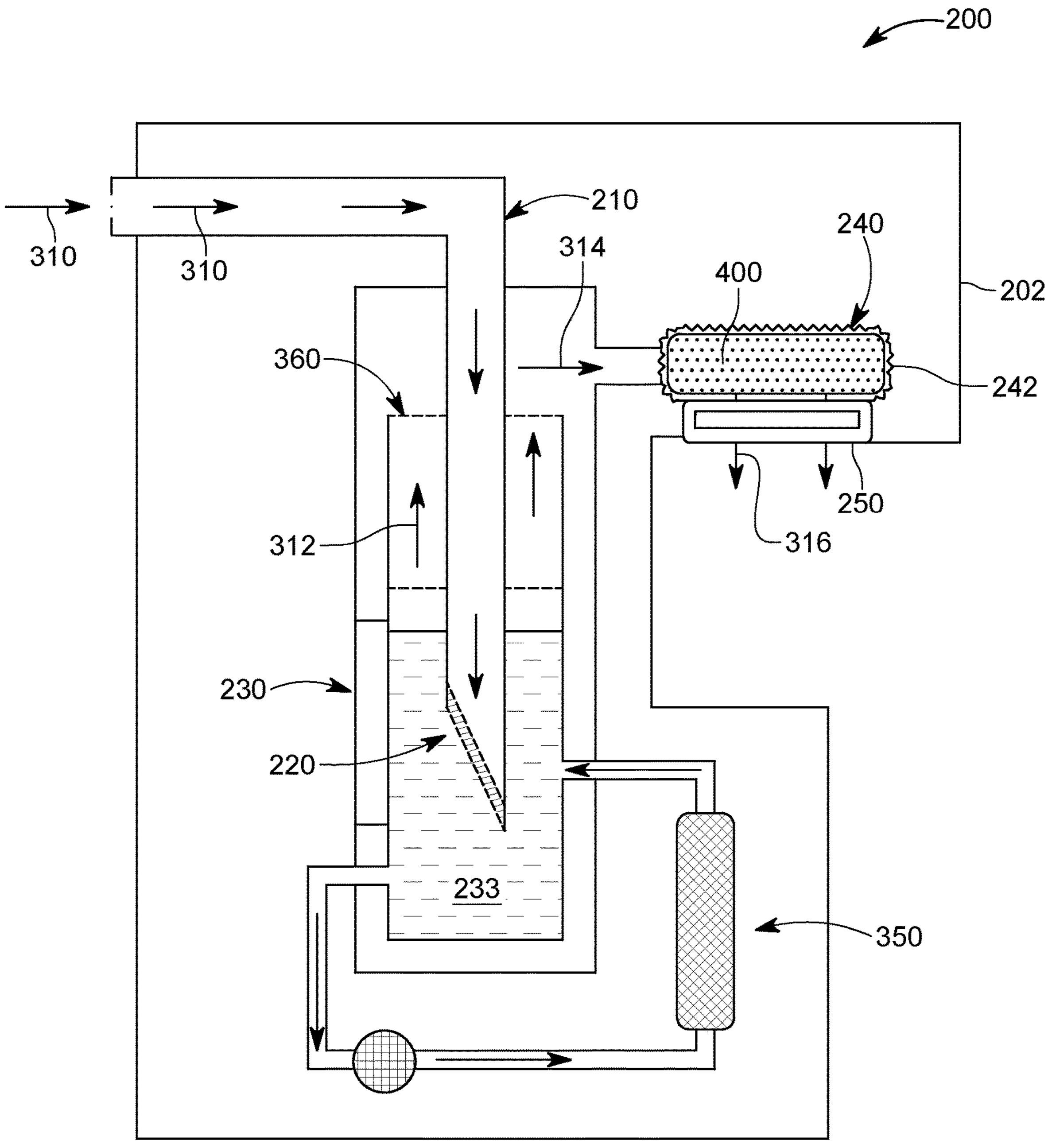
FIG. 4 shows another air breathing filtering system that uses plural filtering stages, one of which is based on a fluid.

In one application, the system 200 is modified to have the entire third stage filtering stage made from a porous material 400, which is coated with an antimicrobial substance, as illustrated in FIG. 4. More specifically, the porous material 400 is manufactured to have small pore sizes to insure complete removal of any virus and bacteria. The porous material pore's size is selected to be large enough to not prohibit the airflow 314 from passing through the filter, but at the same time is smaller than the virus or bacteria's size. The captured/sieved virus on the surface of the porous material can be removed using a disposable filter. The porous material 400 may be placed inside a housing 242, as shown in FIG. 4.

Figure 5A:
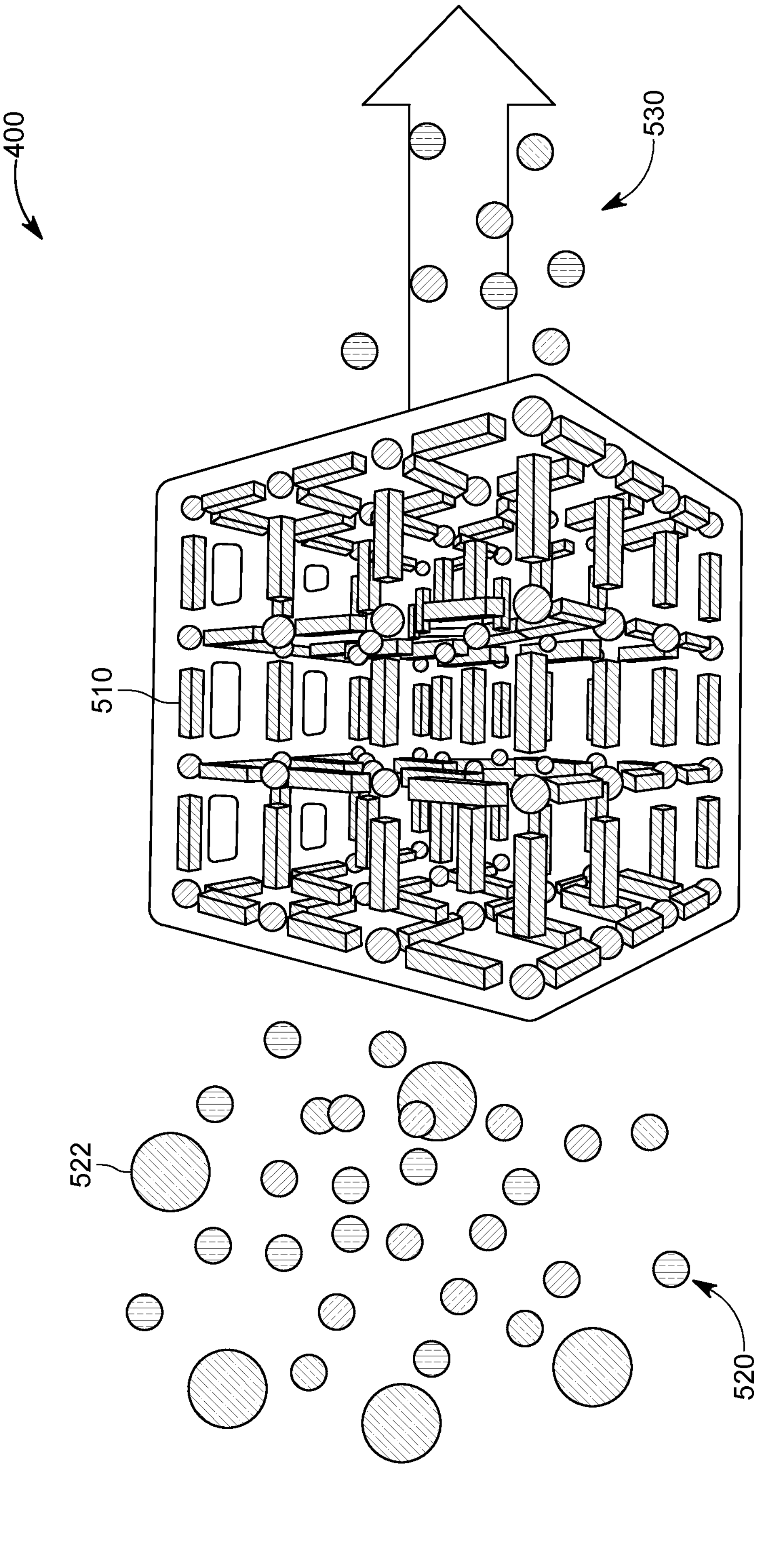
FIG. 5A illustrates a porous material coated with an antibacterial drug and FIG. 5B illustrates how the coating of the porous material with the drug is achieved.

The internal configuration of the porous material 400 is schematically illustrated in FIG. 5A. This figure shows that the porous material 400 is a three-dimensional structure, having plural pores. The pores are coated with an antiviral compound 510. An amalgam of foreign objects 520, including dust, nitrogen, oxygen, water particles, carbon dioxide, and germs 522 pass through the pores of the porous material 400 and directly interact with the antiviral compound 510. The germs are affected by this interaction while the other objects 520 are not. Thus, the stream 530 that exits the porous material 400 has a reduced amount of germs.

Figure 5B:
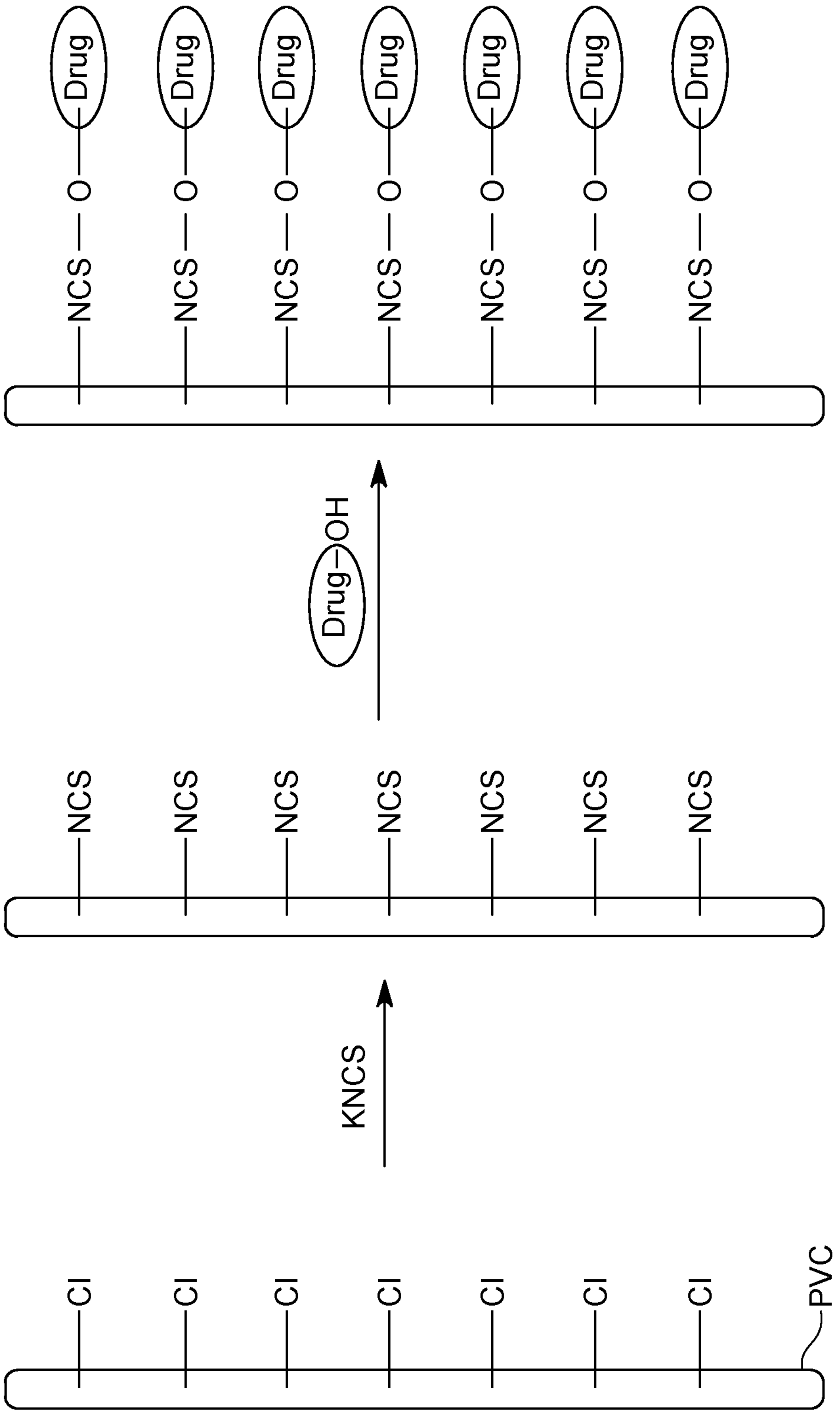

The porous material 400 may also be used to coat an existing filter or any other surface that needs to be conferred antimicrobial properties. For example, a traditional filter may be coated with the porous material 400, like porous silica or porous carbon, or a porous metal-organic framework (MOF) like Fe-MIL-101, UiO-66, etc. For example, hybrid organic—inorganic porous materials such as mesoporous organo-silicates (PMO) are used for drug encapsulation or enzyme immobilization because of the good interactions between their structure and the therapeutic moiety. Thus, such porous materials can be functionalized with selected anti-viral drugs. FIG. 5B illustrates how a PVC porous material is treated with potassium thiocyanate (KNCS) to obtain poly thiocyanate. The poly thiocyanate is then treated with an antimicrobial drug to graft the drug onto the poly thiocyanate material. The PVC and KNCS are just an example of possible materials that can be used to obtain a drug coated material. However, it is possible to coat the anti-viral reagents to the surface of other porous materials. These anti-viral materials can be used to cover the surfaces of not only the filters used in the system 200, but also those of different other places such as desks, chairs, doors and walls in class rooms, lecture halls, offices, meeting rooms, busses, ships and aircrafts, or even on open areas such as metro stations, airports, hospitals corridors and medical centers. As the infection of the surfaces is a problem of major concern, especially due to the Covid-19 pandemic, some of the antiviral compounds discussed herein can be added to paints and then be coated onto the surface of the porous materials, to obtain a desired surface coating.

The system 200 is effective in removing the germs from the incoming air stream 310 because according to World Health Organization (WHO), the SARS-Cov-2 virus can be transmitted through the air droplets. The air droplet can be classified into two main categories, respiratory droplets, when the droplet particles are larger than 5-10 μm in diameter and nuclei droplet, when they are smaller in diameter than 5 μm. The virus survival and transmittal depends on the droplet size, since the virus is primarily transmitted between people through respiratory droplets and direct and indirect contact routes. Thus, using filters (like the porous material 400) with pore sizes less than 5 μm in diameter, and treating the air stream with different antiviral drugs, in addition to exposing the air stream to the liquid phase process in the second filtering stage 230, insure an effective filtering and cleaning of the incoming air stream from any virus. Note that the number of air filtration stages may be increased as necessary.

Because the air stream passes through the liquid 233, which includes highly concentrated antivirus and/or anti-microbial reagents, detergents and alcohols, this system is highly efficient. There are many advantages of the liquid phase, as a mixture of different anti-microbial substances can be added with no limit on their concentration levels as the chamber 234 is fully enclosed. Moreover, the anti-microbial materials can be changed based on the spread out of the different viruses and bacteria. For example, many antiviral drugs have been considered recently for treatments of the Corona virus. A different combination of the antiviral compounds can be added with no limit of the drug concentration and no concern on side effects of these drugs as it will target the virus outside the human body. One advantage of this stage is its flexibility and reliability to be used for different germs and the ability to combine different approaches to eliminate the viruses, bacteria and other microbial species. For example, addition of isopropanol or ethanol with a high concentration can be used to deactivate the COVID-19 virus. Other approaches such as those used in the third filtration stage, or even applying the high temperature, ultrasonication, other mechanical means, thermal and electrical stressor to the fluid 233 to disable the virus can be easily added to the second filtration stage.

Figure 6:
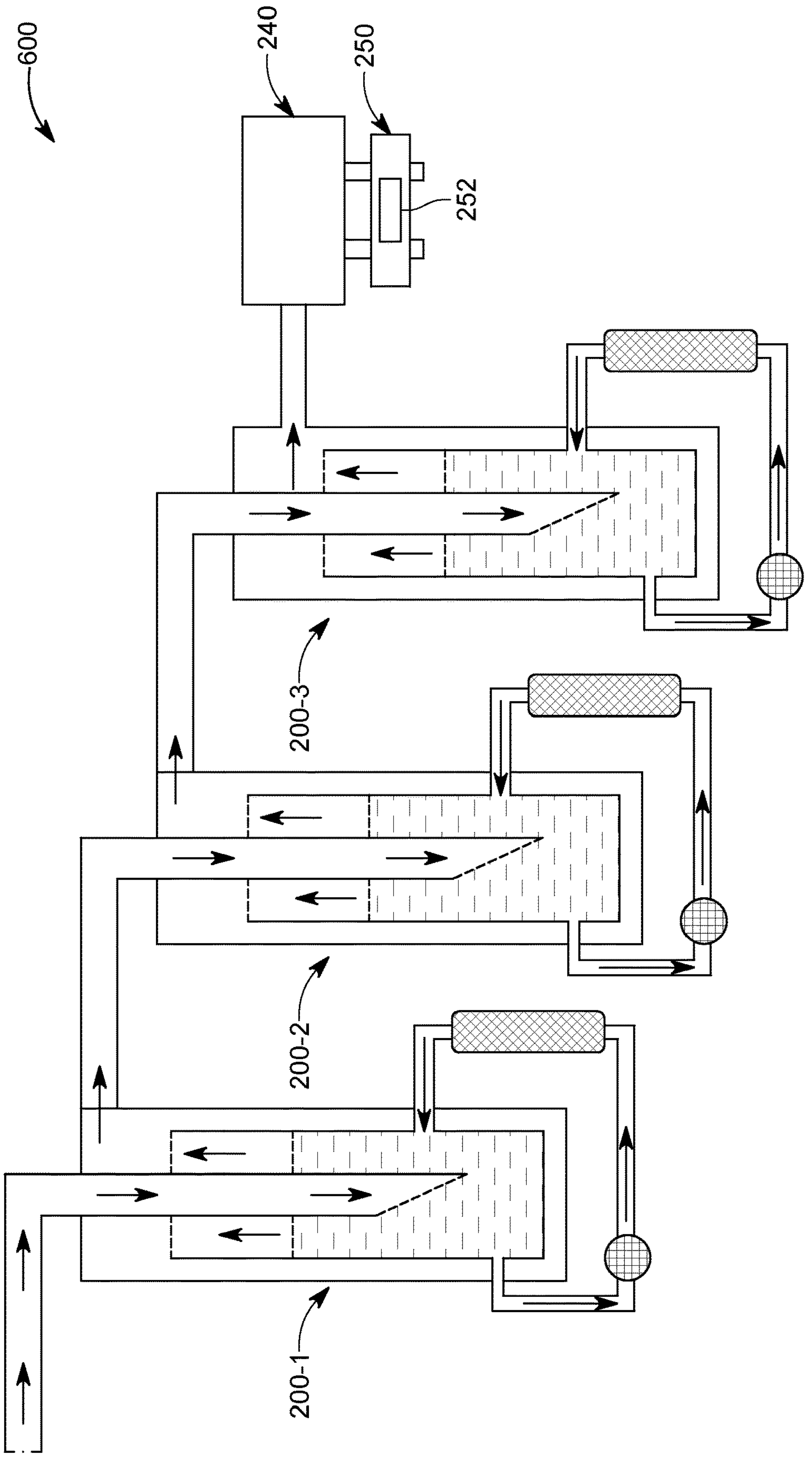
FIG. 6 illustrates multistep air breathing filtering systems connected in series to each other, each one using plural filtering stages, one of which is based on a fluid.

The air breathing filtering system 200 may be connected to similar systems 200, in a cascade arrangement, as shown in FIG. 6, i.e., pairs of the first and last filtering stages of the systems 200 are fluidly connected to each other in series. The compounded system 600 shows only three single systems 200-1 to 200-3 connected in series to each other. However, more or less systems 200 may be connected to each other. In this embodiment, the third filtering stage 240 of the system 200 is removed and the second filtering stage 230 is fluidly connected to the air intake of the next system 200. Only the last system 200-3 has the third filtering stage 240 and the purified air output 250 including the air suction pump 252. The number of single systems 200 that are added to the multi-system 600 varies depending on the desired degree of air purification. The more single systems 200 are added, the better purified is the output air.

Figure 7:
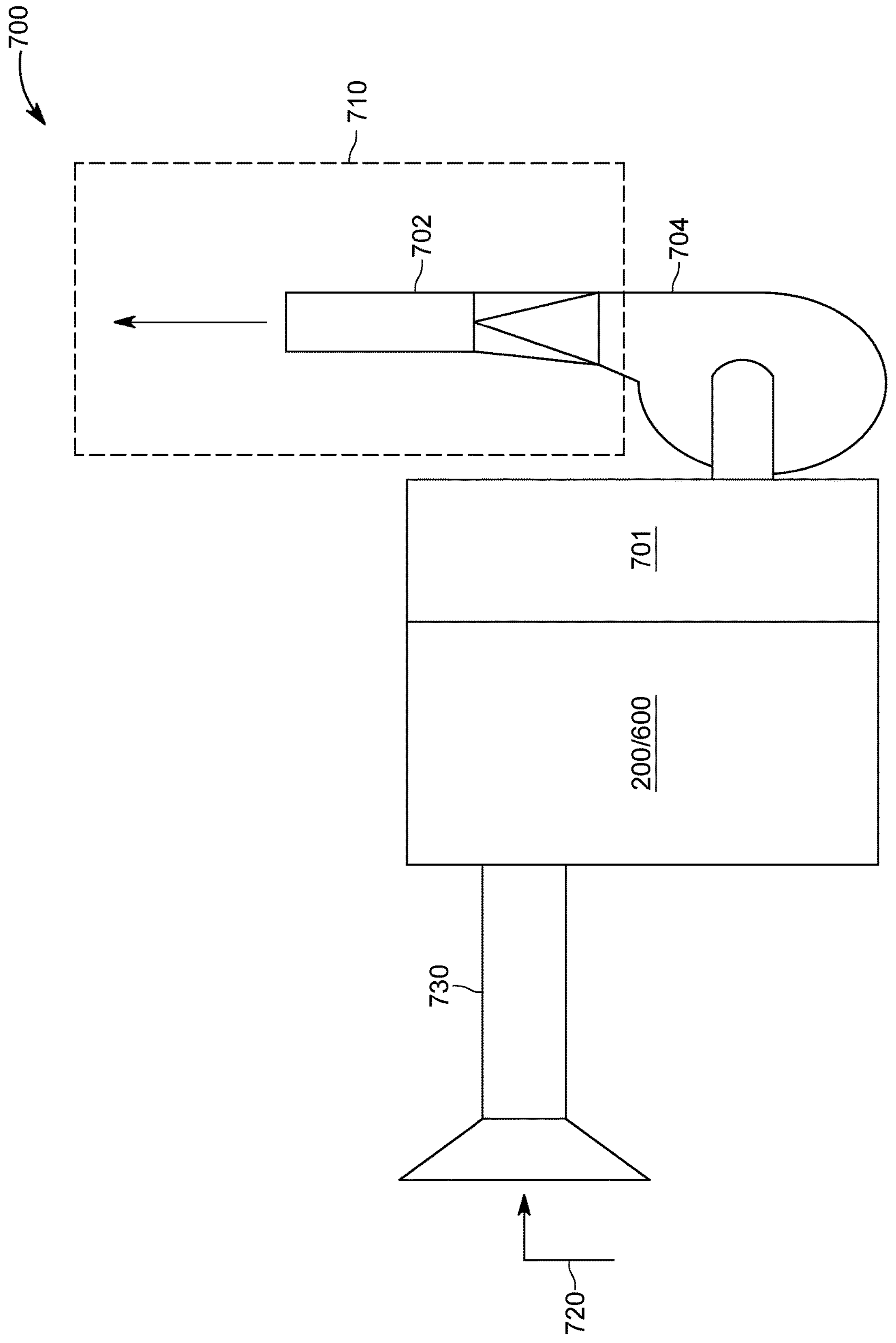
FIG. 7 illustrates an air breathing filtering system being used together with an air conditioning (AC) unit in a stationary enclosure.

The single system 200 or the multiple system 600 can be added to any traditional air conditioning unit to form an AC system for cleaning the air before being heated or cooled. For example, FIG. 7 shows an AC system 700 having a traditional AC unit 701, which is attached to an enclosure 710 (for example, office space, residential space, vehicle, etc.) through a conduit 702. A fan or blower 704 pumps the cooled or heated air inside the enclosure 710. The intake air 720 is taken either from outside the enclosure 710, or from the enclosure, and is provided along another conduit 730 to the system 200 or system 600 discussed above. The air is filtered and then supplied to the AC unit 701 for being heated or cooled. One skilled in the art would understand that the system 200/600 can be retroactively added to any existing AC unit. Thus, the AC system 700 includes the AC unit 701 and the system 200/600.

Figure 8:
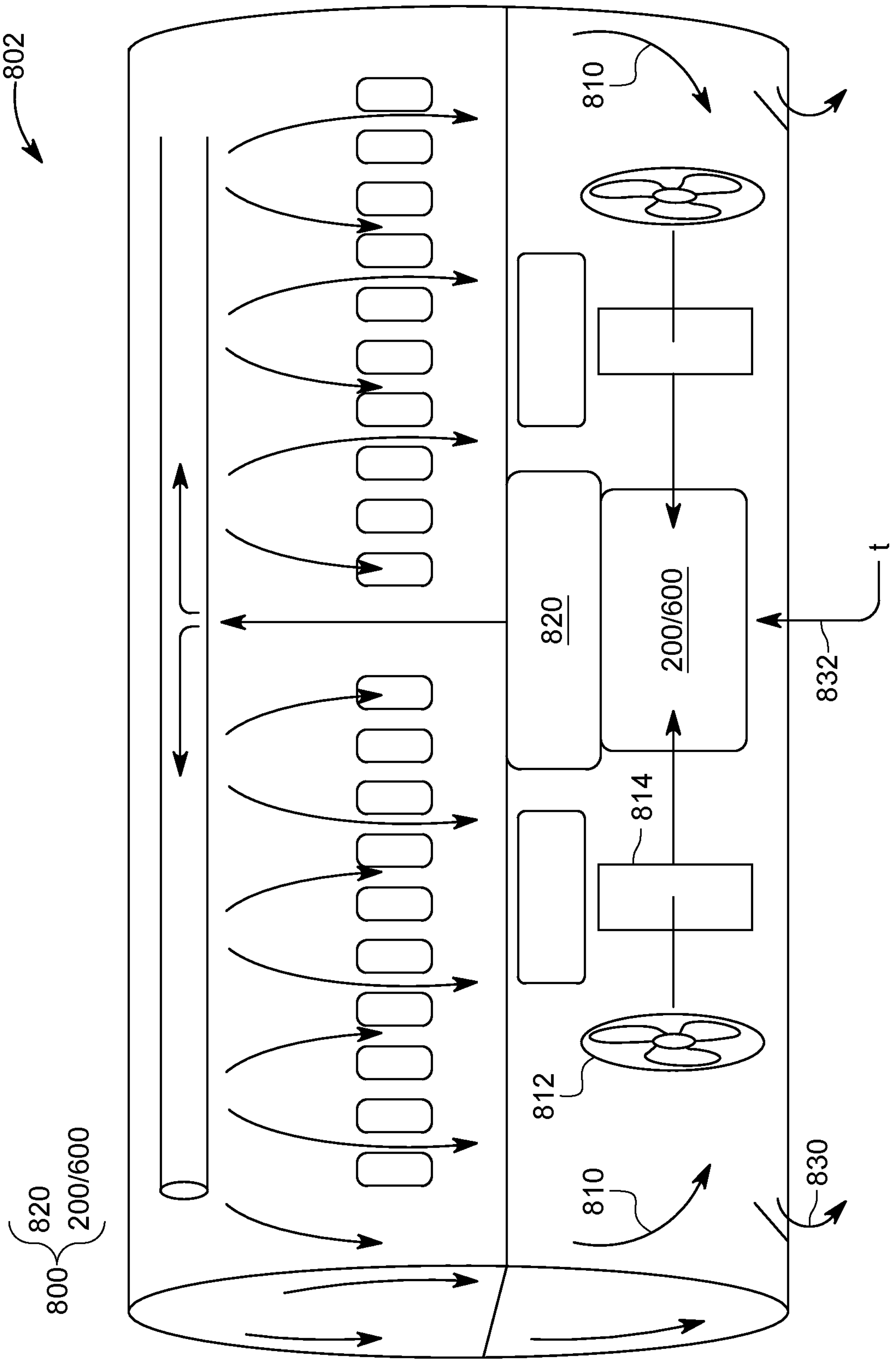
FIG. 8 illustrates an air breathing filtering system being used together with an AC unit in a moving enclosure.

While FIG. 7 shows the system 200/600 being added to a stationary building, FIG. 8 illustrates the capability of the system 200/600 to be added to a moving vehicle, an aircraft 802 in this case. It is noted that the system 200/600 receives the cabin air 810, which is moved by one or more fans 812 through the traditional filters 814. After filtering the air, the system 200/600 sends the purified air to the AC unit 820, which distributes the heated/cooled and purified air back to the cabin. Note that the airplane 802 also discharges some of the air 830 outside the fuselage and takes fresh air 832 from outside the fuselage. Thus, the integrated AC system 800, which includes the AC unit 820 and the system 200/600 is capable of not only heating or cooling the air, but also purifying the air by disabling the germs.

In one application, the system 200/600 is compact and portable because it is a standalone system that can be physically moved from one location, for example, a vehicle, to a second location, for example, a residential space. The system 200/600 just needs to be provided with an intake air stream and its output needs to be fluidly connected to the input of an AC unit or simply to the enclosure for which the air needs to be filtered. The system 200/600 is independent of the AC unit.

Figure 9:
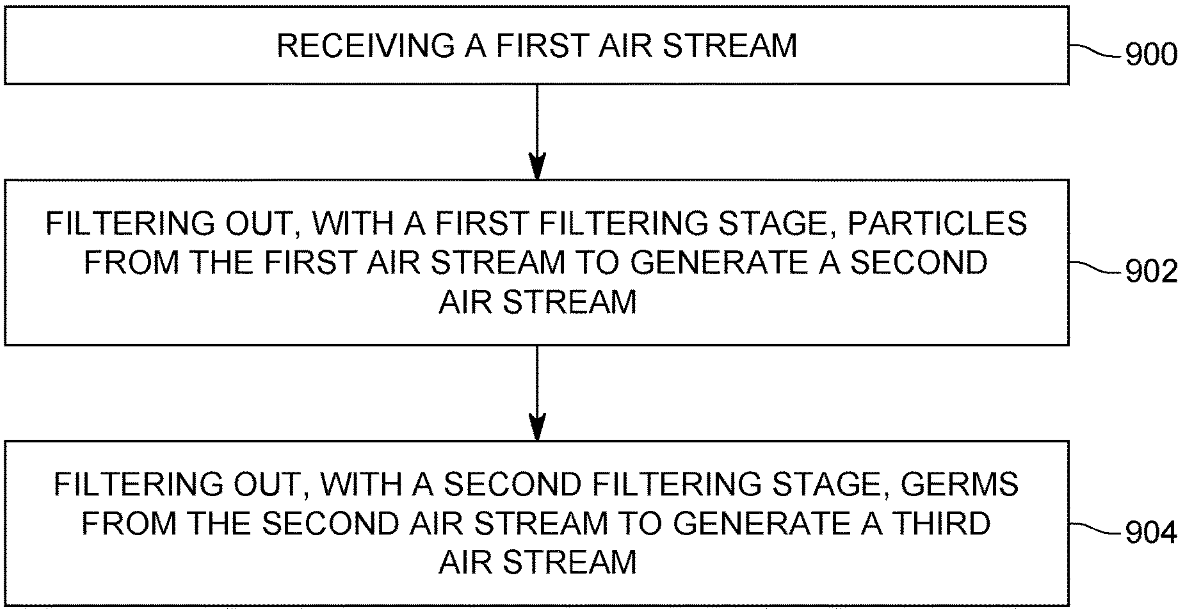
FIG. 9 is a flow chart of a method for disabling germs with an air breathing filtering system that uses a filtering stage based on a fluid.

A method for disabling germs from an air stream by using the system 200/600 is now discussed with regard to FIG. 9. The method includes a step 900 of receiving a first air stream, a step 902 of filtering out, with a first filtering stage, particles from the first air stream to generate a second air stream, and a step 904 of filtering out, with a second filtering stage, germs from the second air stream to generate a third air stream. The second filtering stage uses a different filtering process than the first filtering stage. The second filtering stage uses a liquid to disable the germs from the second air stream.

The disclosed embodiments provide a portable air breathing filtering system that has plural filtering stages, with one of the filtering stage including a liquid filtering process. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. An air breathing filtering system comprising:
- a housing having an air input and an air output;
- a first filtering stage that filters out particles from a first air stream to generate a second air stream;
- a second filtering stage that filters out germs from the second air stream to generate a third air stream, wherein the second filtering stage uses a different filtering process than the first filtering stage;
- a third filtering stage fluidly located between the second filtering stage and the air output, wherein the third filtering stage includes a porous material coated with an antimicrobial drug; and
- a demister located between the second filtering stage and the third filtering stage to remove a vapor from the third air stream,
- wherein the first air stream is received at the air input and the third air stream is discharged outside the housing at the air output, and
- wherein the second filtering stage uses a liquid to disable the germs from the second air stream.

2. The system of claim 1, wherein the first filtering stage includes an air filter having a pore size selected to be in a range of 2-5 μm.

3. The system of claim 1, wherein the second filtering stage comprises:
- a first internal chamber configured to directly receive the first air stream,
- wherein the first internal chamber is configured to hold the liquid.

4. The system of claim 3, wherein the liquid includes an antimicrobial drug that disables germs.

5. The system of claim 3, wherein the liquid includes alcohol that disables germs.

6. The system of claim 3, wherein the liquid includes a detergent that disables germs.

7. The system of claim 3, wherein the liquid includes a bleaching agent that disables germs.

8. The system of claim 3, wherein the liquid includes a chemical compound in a concentration that is harmful to humans.

9. The system of claim 3, wherein the second filtering stage further comprises:
- a second internal chamber that fluidly communicates with the first internal chamber through a filter.

10. The system of claim 3, wherein the second filtering stage further comprises:
- a fluid cleaning system configured to clean the liquid, wherein the fluid cleaning system includes a pump and a filter fluidly connected to the first internal chamber, and located outside the first internal chamber.

11. The system of claim 1, further comprising:
- a purified air output fluidly connected to the second filtering stage, the purified air output including a suction pump that draws the third air stream; and
- a one-way valve located within the first filtering stage to block vapors from the second filtering stage.

12. An air conditioning, AC, system for cooling or heating air, the air conditioning system comprising:
- an AC unit configured to heat or cool an air stream; and
- an air breathing filtering system fluidly attached to the AC unit, and configured to remove germs from the air stream,
- wherein the air breathing filtering system includes,
- a first filtering stage that filters out particles from a first air stream to generate a second air stream; and
- a second filtering stage that filters out germs from the second air stream to generate the air stream, wherein the second filtering stage uses a different filtering process than the first filtering stage,
- wherein the second filtering stage uses a liquid to disable the germs from the second air stream, and
- wherein the air breathing filtering system includes plural pairs of first and second filtering stages fluidly connected to each other in series.

13. The system of claim 12, wherein the second filtering stage comprises:
- a first internal chamber configured to directly receive the first air stream,
- wherein the first internal chamber is configured to hold the liquid.

14. The system of claim 13, wherein the liquid includes an antimicrobial drug, or a drug, or a detergent, or a bleaching agent that disables the germs.

15. The system of claim 13, wherein the liquid includes a chemical compound in a concentration that is harmful to humans.

16. The system of claim 13, wherein the second filtering stage further comprises:
- a second internal chamber that fluidly communicates with the first internal chamber through a filter; and
- a fluid cleaning system configured to clean the liquid, wherein the fluid cleaning system includes a pump and a filter fluidly connected to the first internal chamber, and located outside the first internal chamber.

17. An air breathing filtering system comprising:
- a housing having an air input and an air output;
- a first filtering stage that filters out particles from a first air stream to generate a second air stream;
- a second filtering stage that filters out germs from the second air stream to generate a third air stream, wherein the second filtering stage uses a different filtering process than the first filtering stage, and wherein the second filtering stage comprises:
  - a first internal chamber configured to directly receive the first air stream, wherein the first internal chamber is configured to hold the liquid, and
  - a fluid cleaning system configured to clean the liquid, wherein the fluid cleaning system includes a pump and a filter fluidly connected to the first internal chamber, and located outside the first internal chamber,
- wherein the first air stream is received at the air input and the third air stream is discharged outside the housing at the air output,
- wherein the second filtering stage uses a liquid to disable the germs from the second air stream.

* * * * *